United States Patent [19]
Mackles et al.

[11] Patent Number: 5,322,683
[45] Date of Patent: Jun. 21, 1994

[54] ANHYDROUS AEROSOL FOAM

[76] Inventors: Leonard Mackles, 311 E. 23rd St., New York, N.Y. 10010; Leonard Chavkin, R.D. #1, Box 90, Bloomsbury, N.J. 08804

[21] Appl. No.: 345,827

[22] Filed: May 1, 1989

[51] Int. Cl.$^5$ .................................. A61K 9/12
[52] U.S. Cl. ........................ 424/45; 424/47; 424/70; 424/401; 514/945; 514/966; 514/967
[58] Field of Search ............ 424/45, 47, 70, 401, 424/78.02, 78.07, 78.05, 78.03, DIG. 1; 514/945, 966, 767

[56] References Cited

U.S. PATENT DOCUMENTS

| | | | |
|---|---|---|---|
| 3,135,658 | 6/1964 | Hanus et al. | 424/45 |
| 3,250,680 | 5/1966 | Menkart et al. | 424/56 |
| 3,419,658 | 12/1968 | Sanders | 424/45 |
| 3,770,648 | 11/1973 | Mackles | 252/305 |
| 4,110,426 | 8/1978 | Barnhurst | 424/47 |
| 4,379,143 | 4/1983 | Sherry et al. | 424/684 |
| 4,627,973 | 12/1986 | Moran et al. | 424/47 |
| 4,639,367 | 1/1987 | Mackles | 424/45 |
| 4,656,043 | 4/1987 | Hawkins | 424/70 |
| 4,722,837 | 2/1988 | Cameron | 424/70 |
| 4,752,465 | 6/1988 | Mackles | 424/45 |
| 4,767,463 | 8/1988 | Brode | 424/71 |
| 4,892,727 | 1/1990 | Grollier | 424/70 |
| 4,933,176 | 6/1990 | van Reeth | 424/70 |

OTHER PUBLICATIONS

Soap and Chem. Specialties, Nonaqueous Aerosol Foams, Sanders, 1960.

*Primary Examiner*—Thurman K. Page
*Assistant Examiner*—Raj Bawa
*Attorney, Agent, or Firm*—Omri M. Behr; Matthew J. McDonald

[57] ABSTRACT

There is provided an anhydrous topically applicable aerosol foam composition comprising a foamable anhydrous liquid, a foaming agent selected from the group consisting of methyl glucose $C_{16}$-$C_{18}$ aliphatic acid esters and a propellant, said propellant being capable of existing in gaseous form at ambient pressure and temperature and being present in an amount sufficient to produce a stable measurable foam but insufficient to produce a spray when said composition is ejected through an aerosol valve.

12 Claims, No Drawings

ANHYDROUS AEROSOL FOAM

SUMMARY OF THE INVENTION

There is provided an anhydrous topically applicable aerosol foam composition comprising a foamable anhydrous liquid, a foaming agent selected from the group consisting of methyl glucose $C_{16}$–$C_{18}$ aliphatic acid esters and a propellant, said propellant being capable of existing in gaseous form at ambient pressure and temperature and being present in an amount sufficient to produce a stable measurable foam but insufficient to produce a spray when said composition is ejected through an aerosol valve.

Suitably, the composition comprises from about 35 to about 95% by weight of said foamable anhydrous liquid, from about 0.2 to about 10% by weight of said foaming agent, and from about 2 to about 15% by weight of said propellant, all % being by weight of the total composition. If desired, the composition may additionally comprising between about 0.1 to about 50% by weight of at least one an additional topically active composition which may be a solid suspendable in or a material soluble in the composition. The active component may be a foamable liquid.

BACKGROUND OF THE INVENTION

Non-aqueous aerosol foams have been disclosed heretofore. The selection of suitable foaming agents has however been a problem. U.S. Pat. No. 3,135,658 to Hanus and Oulette, discloses a method of treating bovine mastitis using a milk miscible, non-aqueous surfactant stabilized oleaginous liquid material, which foams upon contact with the milk in the cow's udder. The material which is administered does not, of itself, create a foam. A heat generating composition, one of the uses of the foams disclosed herein, is disclosed in U.S. Pat. No. 3,250,680 to Menkart and Ricciuti. This material is not a foam but utilizes aluminosilicate molecular sieve materials taken up in non-aqueous carriers such as polyethylene glycol, using sorbitan monostearate or polyoxyethylene sorbitan mono oleate as surfactant materials in the composition.

The first true non-aqueous aerosol foam is disclosed in U.S. Pat. No. 3,419,658 to Sanders. The Sanders foam however is limited to white mineral oil as the anhydrous liquid. The surfactants are also rather limited to their particular category. It should be noted that the same author published a somewhat extensive review of non-aqueous aerosol foams in *Soap and Chemical Specialties*, November 1960, page 87 through 109. White Sanders projects several uses for such materials, the non-aqueous liquids are limited to alkylene glycols and the ethers thereof. Furthermore, the surfactants are similarly of the propylene glycol monostearate or polyoxyethylene sorbitan monostearate type.

U.S. Pat. No. 3,770,648 to Leonard Mackles (one of the inventors herein) is directed to an aerosol foam utilizing a silicone resin as the foaming agent. U.S. Pat. No. 4,379,143 to Sherry, et al., is directed to a topical self-heating liquid or ointment used for analgesic purposes which comprises a zeolite and an anhydrous liquid. There is no disclosure in Sherry of the possibility of foaming the compositions since no foaming agent is disclosed. Furthermore, the invention is specifically limited to the use of the zeolite as the sole warming agent. U.S. Pat. No. 4,627,973 to Moran, et al., is directed to a skin mousse. Moran, et al., however comprises a substantial amount of water and cannot therefore be considered to fall within the category of the present invention.

U.S. Pat. No. 4,639,367 to Leonard Mackles is directed to an edible anhydrous aerosol foam composition comprising a foamable liquid oil, a dispersed solid, a foaming agent and a propellent. However, the disclosure of this invention being directed to edible foams, does not consider the requirements necessary for foaming a topically absorbable, as opposed to an ingestible, anhydrous liquid.

U.S. Pat. No. 4,752,465, which is a continuation-in-part of the aforementioned U.S. Pat. No. 4,639,367, is directed to a similar product having dispersed therein a particular proportion of solid particles.

It will thus be seen that the problem of providing an anhydrous topically applicable aerosol foam containing a foamable topically absorbable anhydrous liquid, has not been satisfactorily addressed by the prior art. In order to provide commercially satisfactory products in the aforementioned category, it is necessary that foams be preparable from a diverse group of anhydrous liquids such as glycerol fatty acid esters; e.g., soybean oil, corn oil, mono and diglycerol esters, acetylated monoglycerides, glyceryl triacetate; di and triethyl esters of organic acids, e.g., triethyl citrate, diethyl phthalate; aromatic acid esters, e.g., methyl salicylate, benzyl benzoate; and water soluble glycols, e.g., propylene glycol sand polyethylene glycol 400.

While the art, as shown by the aforementioned references, teaches a large number of foaming agents, it has been our surprising finding that these foaming agents are not satisfactory for foaming all of the aforementioned anhydrous liquids.

DESCRIPTION OF THE PREFERRED EMBODIMENTS

Among the preferred foamable liquids there by be mentioned glycerol fatty acid esters, such as glyceryl triacetate, acetylated mono glycerides, di- and tri-ethyl esters of organic hydrocarbon acids, such as diethyl phthalate, triethyl citrate, monoesters of aromatic monocarboxylic acids such as methyl salicylate, benzyl benzoate and water soluble glycols such as propylene glycol or polyethylene glycol 400.

We have found that methyl glucose sesquiester of stearic acid is a highly useful foaming agent for aerosol foam systems. The ester is formed by reacting methyl glucoside and stearic acid in correct proportions so as to form the "sesqui" ester having approximately the following properties:

| | |
|---|---|
| Acid value: | 8 max. |
| Saponification value: | 125–140 |
| Hydroxyl Value: | 270–305 |
| Iodine value: | 1 max. |
| HLB: | 6 |
| Appearance: | Off white solid |

Utilizing this foaming agent, methyl glucose sesquistearate at levels between 0.2–10.0% in combination with a suitable foamable anhydrous liquid and an aerosol propellent, there can be obtained a variety of foams suitable for topical application to the dermal and mucosal tissues such as cosmetics, toiletries or drugs. These foams can be made as stiff or as soft as required by simply varying the percentage of methyl glucose sesquistearate used.

In addition to the aforementioned methyl glucose sesquistearate, methyl glucose dioleate is a preferred foaming agent.

The preferred propellants are hydrocarbon propellants such as propane, butane, isobutane and combinations thereof, fluorocarbon propellants such as Freon 11, Freon 12, Dymel 152, Dymel 142 and the like, dimethyl ether and compressed gases such as carbon dioxide, nitrogen and nitrous oxide, 3–10% by weight of propellant being preferred.

Where the foamable liquid itself is not topically active, it is desirable that the composition comprise at least one such agent such as topical anesthetics or analgesics such as menthol, methyl salicylate, benzocaine, or lidocaine, antimicrobials such as benzethonium chloride, benzalkonium chloride, antibiotics such as bacitracin, polymyxin B or streptomycin; enzymes such as streptokinase, trypsin; heat generating agents such as activated sodium aluminum silicate; skin and hair conditioners such as lanolin and stearalkonium chloride; colorants such as RD & C Red 10 Lake, FD & C Yellow #6 Lake and fragrances such as citrus and floral volatile oils.

The foregoing components are listed for purposes of exemplification and not limitation. The invention may be best illustrated by the following working examples.

EXAMPLES

EXAMPLE 1

Topical Analgesic Foam Rub

| | |
|---|---|
| Triethyl Citrate | 55.00% |
| Methyl Salicylate | 30.00 |
| Methyl Glucose Sesquistearate | 5.00 |
| Propellant A-46 (Propane, Isobutane Mixture) | 10.00 |
| | 100.00% |

All percentages are by weight.

Procedure: Heat the triethyl citrate, methyl salicylate and methyl glucose sesquistearate to 60° C., cool with stirring. Submit for aerosol filling. Add the propellant by pressure filling.

The resultant foam is white and dense. It is easily rubbed on body areas in need of analgesia.

EXAMPLE 2

Anal Cleansing Foam

| | |
|---|---|
| Glyceryl triacetate | 92.00% |
| Methyl glucose sesquistearate | 3.00 |
| Propane | 5.00 |
| | 100.00% |

All percentages are by weight.

Procedure: Heat the glyceryl triacetate and methyl glucose sesquistearate to 60° C. Cool with stirring. Submit for aerosol filling. Add the propellant by pressure filling.

The resultant foam is applied to toilet tissue and then used for anal cleansing. The foam being anhydrous will not cause the toilet tissue to tear.

EXAMPLE 3

Medicated Anal Cleanser Foam

| | |
|---|---|
| Glyceryl triacetate | 88.00% |
| Benzocaine | 5.00 |
| Methyl glucose sesquistearate | 2.00 |
| Propane | 5.00 |
| | 100.00% |

All percentages are by weight.

Procedure: Heat the glyceryl triacetate, benzocaine and methyl glucose sesquistearate to 60° C. Cool with stirring. Submit for aerosol filling. Add the propellant by pressure filling.

The resultant foam is applied to toilet tissue and then used for anogenital area cleansing and relief of hemorrhoidal pain. The foam, being anhydrous, will not cause the toilet tissue to tear.

EXAMPLE 4

Vaginal Deodorant Foam Wipe

| | |
|---|---|
| Propylene glycol | 91.90% |
| Benzethonium chloride | 0.10 |
| Methyl glucose sesquistearate | 5.00 |
| Propane | 3.00 |
| | 100.00% |

All percentages are by weight.

Procedure: Heat propylene glycol, benzethonium chloride and methyl glucose sesquistearate to 60° C. Cool with stirring. Submit for aerosol filling. Add propellant by pressure filling.

The resultant water soluble foam can be used on toilet tissue or by hand application to cleanse and deodorize the vaginal area.

EXAMPLE 5

Hot Oil Hair Conditioner Foam

Self Heating Foam

| | |
|---|---|
| Triethyl citrate | 20.00% |
| Acetylated mono glyceride | 22.20 |
| Methyl glucose sesquistearate | 3.00 |
| Solulan 98 (fatty ester-ether lanolin complex) | 1.00 |
| Bentone 38 (quaternium-18-Hectorite) | 1.50 |
| Valfor G-110 (anhydrous sodium aluminosilicate) | 40.00 |
| Isopropyl myristate | 2.00 |
| Fragrance | 0.3 |
| Propellant A-31 (isobutane) | 10.00 |
| | 100.00% |

All percentages are by weight.

Procedure: Heat triethyl citrate, acetylated monoglyceride, methyl glucose sesquistearate, solulan 98 and isopropyl myristate to 70° C. With high speed stirring, add the Bentone 38 and Valfor G-110. Cool with stirring to 40° C., add fragrance and continue stirring until cool. Submit for aerosol filling. The propellant pressure is filled.

This foam is applied to a previous shampooed head while the hair is still wet. The foam will generate heat due to the exothermic reaction between the Valfor G-110 and water. The heat promotes the penetration of the oils into the hair and scalp, giving a conditioning effect to both. The product is rinsed off with water and the hair is then dried.

EXAMPLE 6

Hot Oil Facial Cleanser Foam

Self Heating Foam

| | |
|---|---|
| Acetylated Monoglycerides | 22.00% |
| Methyl glucose sesquistearate | 3.00 |
| Isopropyl myristate | 15.70 |
| Apricot kernel oil | 0.10 |
| Mink oil | 0.10 |
| Bentone 38 (quaternium 18-Hectorite) | 1.50 |
| Valfor G-110 (anhydrous sodium aluminosilicate) | 46.80 |
| PEG 600 Dilaurate | 3.50 |
| Fragrance | 0.30 |
| Propane | 7.00 |
| | 100.00% |

All percentages are by weight.

Procedure: Heat the acetylated monoglycerides, methyl glucose sesquistearate, isopropyl myristate, apricot kernel oil, mink oil and PEG 600 Dilaurate to 60° C. With high speed agitation, add the Bentone 38 and the Valfor G-110. Cool with stirring to 40° C., add fragrance and continue stirring until cool. Submit for aerosol filling. Add propellant by pressure filling.

This foam is applied to the wet face after washing with soap and water. Heat is generated by the exothermic reaction between the Valfor G-110 and the water on the skin. The hot oils will penetrate into the skin pores to remove make-up, debris and dirt. The product is then rinsed off for a feeling of deep cleansing.

EXAMPLE 7

Self-Heating Analgesic Foam Rub

| | |
|---|---|
| Menthol | 2.00% |
| Diethyl phthalate | 52.50 |
| Methyl glucose sesquisterate | 0.50 |
| Polyethylene glycol 400 dioleate | 2.00 |
| Valfor G-110 (anhydrous sodium aluminosilicate) | 40.00 |
| Propane | 3.00 |
| | 100.00% |

All percentages are by weight.

Procedure: Heat the menthol, methyl salicylate, diethyl phthalate, polyethylene glycol 400 di oleate and methyl glucose sesquistearate to 60° C. With high speed stirring, add the Valfor G-110 and cool to room temperature. Submit for aerosol filling. Add the propellant by pressure filling.

The resultant foam is white and non-greasy. When applied to the skin, the Valfor G-110 reacts exothermically with the moisture in the skin, giving an immediate sensation of heat, which leads to better penetration of the analgesic actives and a more pronounced feeling of relief. The addition of the polyethylene glycol 400 dioleate allows the moisture of the skin to more easily mix with the foam.

EXAMPLE 8

Self-Heating Analgesic Foam Rub

| | |
|---|---|
| Menthol | 2.00% |
| Diethyl phthalate | 52.00 |
| Methyl glucose dioleate | 1.00 |
| Polyethylene glycol 400 dioleate | 2.00 |
| Valfor G-110 (anhydrous sodium aluminosilicate) | 40.00 |
| Propane | 3.00 |
| | 100.00% |

All percentages are by weight.

Procedure: Mix the menthol, methyl salicylate, diethyl phthalate, polyethylene glycol 400 dioleate and methyl glucose dioleate till clear. With high speed stirring, add the Valfor G-110 until mixture is uniform. Submit for aerosol filling. Add the propellant by pressure filling.

The resultant foam is white and non-greasy. When applied to the skin, the Valfor G-110 reacts exothermically with the moisture in the skin, giving an immediate sensation of heat, which leads to better penetration of the analgesic actives and a more pronounced feeling of relief. The addition of the polyethylene glycol 400 dioleate allows the moisture of the skin to more easily mix with the foam.

EXAMPLE 9

Self-Heating Analgesic Foam Rub

| | |
|---|---|
| Menthol | 2.00% |
| Methyl salicylate | 3.00 |
| Diethyl phthalate | 52.50 |
| Methyl glucose sesquistearate | 0.50 |
| Polyethylene glycol 400 dioleate | 2.00 |
| Valfor G-110 (anhydrous sodium aluminosilicate) | 40.00 |
| Propane | 3.00 |
| | 100.00% |

All percentages are by weight.

Procedure: Heat the menthol, methyl salicylate, diethyl phthalate, polyethylene glycol 400 dioleate and methyl glucose sesquistearate to 60° C. With high speed stirring, add the Valfor G-110 and cool to room temperature. Submit for aerosol filling. Add the propellant by pressure filling.

The resultant foam is white and non-greasy. When applied to the skin, the Valfor G-110 reacts exothermically with the moisture in the skin, giving an immediate sensation of heat, which leads to better penetration of the analgesic actives and a more pronounced feeling of relief. The addition of the polyethylene glycol 400 dioleate allows the moisture of the skin to more easily mix with the foam.

EXAMPLE 10

Self-Heating Analgesic Foam Rub

| | |
|---|---|
| Menthol | 2.00% |
| Methyl salicylate | 3.00 |
| Diethyl phthalate | 52.00 |
| Methyl glucose dioleate | 1.00 |
| Polyethylene glycol 400 dioleate | 2.00 |
| Valfor G-110 (anhydrous sodium aluminosilicate) | 40.00 |
| Propane | 3.00 |
| | 100.00% |

All percentages are by weight.

Procedure: Mix the menthol, methyl salicylate, diethyl phthalate, polyethylene glycol 400 dioleate and methyl glucose dioleate till clear. With high speed stirring, add the Valfor G-110 and mix till uniform. Submit for aerosol filling. Add the propellant by pressure filling.

The resultant foam is white and non-greasy. When applied to the skin, the Valfor G-110 reacts exothermically with the moisture in the skin, giving an immediate sensation of heat, which leads to better penetration of the analgesic actives and a more pronounced feeling of relief. The addition of the polyethylene glycol 400 dioleate allows the moisture of the skin to more easily mix with the foam.

EXAMPLE 11

Sunscreen Foam

| Octyl Diethyl PABA | 7.00% |
|---|---|
| Benzyl benzoate | 10.00 |
| Methyl glucose sesquistearate | 3.00 |
| Soybean Oil w/antioxidant BHA | 76.70 |
| Fragrance | 0.30 |
| Propane | 3.00 |
| | 100.00% |

All percentages are by weight.

Procedure: Heat the octyl dimethyl PABA, benzyl benzoate, methyl glucose sesquistearate and soybean oil to 60° C. Cool with stirring and submit for aerosol filling. Add propellant by pressure filling.

The foam is white and easily spread on the skin. Since the foam is anhydrous and hydrophobic, it is very resistant to washing off during swimming.

We claim:

1. An anhydrous topically applicable aerosol foam composition comprising
   a) a foamable topically absorbable anhydrous liquid, selected from the group consisting of glycerol fatty acid esters, acetylated monoglycerides, di- and triethyl esters of organic hydrocarbon acids, monoesters of aromatic monocarboxylic acids and water soluble glycols,
   b) a foaming agent selected from the group consisting of methyl glucose $C_{16}$–$C_{18}$ aliphatic acid esters and
   c) a propellant,
   said propellant being capable of existing in gaseous form at ambient pressure and temperature and being present in an amount sufficient to produce a stable measurable foam but insufficient to produce a spray when said composition is ejected through an aerosol valve.

2. A composition of claim 1 comprising:
   about 35 to about 95% by weight of the total composition of said foamable anhydrous liquid,
   about 0.2 to about 10% by weight of the total composition of said foaming agent,
   and about 2 to about 15% by weight of the total composition of said propellant.

3. A composition of claim 2 comprising:
   about 3 to about 10% by weight of the total composition of said propellant.

4. A composition of claim 1 additionally comprising between about 0.1 to about 50% by weight of the total composition of a topically applicable pharmacologically active composition of at least one component.

5. A composition of claim 4 wherein the topically applicable pharmacologically active composition comprises a solid suspendable in or a material soluble in the total composition.

6. A composition of claim 5 comprising at least one member of the group consisting of topical anesthetics, analgesics, antimicrobials, antibiotics, enzymes, heat generating agents, skin and hair conditioners, colorants and fragrances.

7. A composition of claim 1 wherein the foaming agent is selected from the group consisting of methyl glucose sesquistearate and methyl glucose dioleate.

8. A composition of claim 1 wherein the propellant is selected from the group consisting of aliphatic hydrocarbon propellants, fluorocarbons, dimethyl ether propellants, carbon dioxide, nitrogen and nitrous oxide.

9. A composition of claim 1 wherein the propellant is selected from the group consisting of aliphatic hydrocarbon propellants.

10. A composition of claim 1 wherein the propellant is propane.

11. A composition of claim 1 wherein the foamable liquid comprises at least one member selected from the group consisting of glycerol fatty acid esters, di-and tri-ethyl esters of organic hydrocarbon acids, monoesters of aromatic monocarboxylic acids, and water soluble glycols.

12. A composition of claim 1 wherein the foamable liquid comprises at least one component which is a topically active substance.

* * * * *